United States Patent [19]

Dallal et al.

[11] Patent Number: 5,059,414

[45] Date of Patent: Oct. 22, 1991

[54] MULTI-PHASE HIGH VISCOSITY COSMETIC PRODUCTS

[75] Inventors: Joseph A. Dallal, Bridgeport; Teresa Ferullo, Wilton; Cheryl M. Kurzyn, Norwalk, all of Conn.

[73] Assignee: Shiseido Co. Ltd., Tokyo, Japan

[21] Appl. No.: 214,533

[22] Filed: Jul. 1, 1988

[51] Int. Cl.$^5$ .................. A61K 7/075; A61K 7/11
[52] U.S. Cl. ......................... 424/70; 924/71; 924/78; 924/DIG.2; 924/401; 252/DIG.13; 514/944
[58] Field of Search ............ 424/70, DIG. 2, 71, 424/78, 486, 487, 488, 401; 252/DIG. 13; 514/944

[56] References Cited

U.S. PATENT DOCUMENTS 3,427,382  2/1969  Haefele .................. 424/71
4,839,166  6/1989  Grollier et al. ........ 424/78 X

FOREIGN PATENT DOCUMENTS 1709927  2/1986  European Pat. Off. .
2107586  5/1983  United Kingdom .

Primary Examiner—Thurman K. Page
Assistant Examiner—Susan S. Rucker
Attorney, Agent, or Firm—Melvin I. Stoltz

[57] ABSTRACT

By combining two or more separate and distinct cosmetic preparations in independent gelling matrices to obtain a plurality of phases and combining the plurality of previously incompatible phases into a single container, a multi-phase, high viscosity cosmetic product is attained which assures that all phases are simultaneously dispensed from the container in a repeatable, consistent, metered ratio. By employing the present invention, a combined styling and conditioning product is achieved as well as a combined shampoo and conditioning product and a combined conditioner/conditioner for the face, hands or hair. In addition, the multi-phase, high viscosity cosmetic products of the present invention are preferably constructed with each of these phases being visually distinctive from each of the other phases, thereby providing a readily indentifiable and visually distinctive and pleasing appearance.

10 Claims, No Drawings

MULTI-PHASE HIGH VISCOSITY COSMETIC PRODUCTS

TECHNICAL FIELD

This invention relates to a multi-phase high viscosity cosmetic product wherein all phases are dispensed simultaneously, with their individual characteristics retained. More specifically, this invention relates to multi-phase high viscosity cosmetic products in the hair care field, and formulation therefor.

BACKGROUND ART

Due to socially derived fashion and good hygiene, it has long been common for human hair to be styled and cleaned. With the variety of hair lengths, hair treatments and visual appearances which exist, styling aids have long been employed to attain the desired finished effect. Among these aids are specialty shampoos, treatments, rinses, combing aids, setting aids, sculpting aids, and finishing aids, all designed to prepare the hair or change the consistency of the hair to respond to a styling technique to attain a particular desired effect.

In general, regardless of the particular visual effect to be obtained, a cleansing and styling cycle is required to prepare the hair and finish the hair in the desired manner, whether the final effect is to be soft and flowing, or stiff and rigid, with either a natural or plastique look. Except for special designer effects, it is generally accepted that the cleansing/styling cycle should leave the hair with high luster and sheen, as well as with a full bodied appearance, with the hair being easily managed for being placed into the desired style.

In order to satisfy the requirements for the cleansing/styling cycle, many commercially available products have been formulated for complementing each other, such as cleansing shampoos and cream rinses, and stiff setting gels and glossing aids. In addition, fragrance, color, rheology, clarity, sparkle and other physical and organoleptic characteristics are utilized to win consumer enticement or acceptance, to provide actual or final function, or to provide mechanical means to create the desired function.

Although numerous hair care products have been developed and are employed simultaneously with other, complementary products, these products are all produced and distributed as separate, independent products. One principal example of such complementary products is the styling or sculpting gels have been created and employed for holding the hair in a particular place in accordance with the desired style. As the complementary product, glossing and conditioning agents have been employed with the sculpting gels in order to give a finished style and impart a fresh, healthy appearance to the hair.

Due to the composition of these products, sculpting gels and glossing/conditioning agents have been sold as separate, independent products, which may be mixed together prior to application to the hair. However, a combined sculpting gel and glossing/conditioning agent has not been obtainable, in view of the inability to assure product separation and precise dispensing of the requisite ratio of each product.

Therefore, it is a principal object of the present invention to provide a multi-phase, high viscosity cosmetic preparation wherein said preparation comprises two or more independent, rheologically unique components which are maintained in a single container and simultaneously dispensed therefrom in a preset, desired, continuously repeated ratio.

Another object of the present invention is to provide a multi-phase, high viscosity cosmetic preparation having the characteristic features described above, wherein each of said phases are maintained independent from each other, regardless of external forces acting thereon to cause interaction therebetween.

Another object of the present invention is to provide a multi-phase, high viscosity cosmetic preparation having the characteristic features described above, wherein said phases are mixable with each other upon rubbing, but are retained separate and distinct during retention in the dispenser.

Other and more specific objects will in part be obvious and will in part appear hereinafter.

DETAILED DESCRIPTION OF THE INVENTION

The present invention overcomes the prior art difficulties by combining two or more generally incompatible products into a single container in a manner which assures that both products are simultaneously dispensed from the container in a repeatable, consistent, metered ratio. As defined herein, the components of the multi-phase, high viscosity cosmetic preparation of the present invention provides product formulations which assure that each of the products or phases contained in the multi-phase formula retain their individual characteristics during the entire time these products or phases remain in the container.

In addition to providing a single container in which the multi-phase components of the cosmetic preparation of the present invention are based, the present invention also assures that each independent phase of the multi-phase cosmetic preparation of this invention is dispensed simultaneously with all of the other phases in a pre-defined, metered ratio. In this way, the precise amount of each product or phase contained within the multi-phase cosmetic preparation of this invention is consistently and repeatedly provided to the user. As a result, substantial added convenience is attained, as well as ease of use, with repeatability of results being assured.

Furthermore, by incorporating two or more independent products into a single container, the resulting multi-phase cosmetic preparation can be presented in a variety of unique forms, thereby establishing any particular desired visual presentation in a highly distinctive and readily identifiable appearance. In particular, if desired, the multi-phases can be arranged in a plurality of alternating stripes, or in various other distinctive aesthetically pleasing arrangements, such as swirls, interleaved, sinusoidal shaped waves, etc. In addition, a single color matrix could be presented on the outer circumference of the packaging, while the alternate phase products are incorporated in the core of the dominant phase, thereby being visually apparent during the dispensing of the multi-phase cosmetic preparation.

Although the multi-phase, high viscosity cosmetic preparation of the present invention can be constructed using numerous alternative complementary products to form the single, multi-phase product of this invention, this disclosure will detail one particular embodiment for a multi-phase high viscosity cosmetic preparation. In this particular embodiment, a sculpting gel for placing and holding the hair is disclosed in combination with a glossing/conditioning agent, employed to give hair the finished style and a healthy fresh appearance. In this way, a combined styling and conditioning product is attained as two phases of a high viscosity cosmetic preparation, which will provide the precisely desired metered ratioed amount of each phase to the consumer, each time the dispenser is activated. Furthermore, as is detailed below, the two phases are constructed with contrasting visual appearances, so that the entire multiphase high viscosity cosmetic preparation of this invention attains a highly distinctive, unique appearing product, to further heighten consumer interest and excitement.

In the preferred embodiment, the sculpting phase of the cosmetic preparation of the present invention comprises a clear, continuous gel which incorporates a setting, film-forming resin and film modifying agents combined in a matrix of a gelling agent. In direct contrast with this clear, continuous gel, the glossing/conditioning phase comprises an opaque gel formed from a detactifying and glossing polymer with dispersing agents, all combined in a matrix of a gelling agent.

Preferably, when these two phases are combined to form this embodiment of the high viscosity cosmetic preparation of the present invention, the glossing/conditioning phase is formed with a particular distinctive color, such as white, and positioned in the container as vertical stripes arranged about the cylindrical dispensing container. In this way, the contrasting opaque color of the glossing/conditioning phase is readily apparent and forms a distinctive contrast to the the substantially transparent or translucent sculpting phase.

Furthermore, in view of the contrast between the opaque coloring of the glossing/conditioning phase and the substantially translucent nature of the sculpting phase, a three-dimensional presentation is achieved which allows the consumer to see through the continuous phase to see the vertical stripes of the glossing/conditioning phase formed about the opposed surfaces of the container. However, as would be obvious to one of ordinary skill in the art, the visual appearance of these phases can be varied using alternate colors, sparkles, or alternately spaced clear or opaque contrasting phases.

As is further detailed below, the ratio of the two phases can be varied to achieve a particular styling, glossing and conditioning effect for any particular hair or style types. Although the compositions of this embodiment of the present invention, as detailed below, has been constructed to attain product acceptable to the majority of consumers, it would be apparent to one of ordinary skill in the art that alternate ratios could be employed, such as incorporate a larger quantity of the glossing/conditioning phase to attain a product specially formulated for dry and damaged hair or coarse and wiry hair.

Alternatively, the sculpting phase could be increased in order to have a product formulated for fine and limp hair. Furthermore, various styles from stiff to soft can be satisfied by alternate product formulations wherein the concentration of the products are varied in order to achieve these particular results.

SCULPTING PHASE

The sculpting phase of this embodiment of the multiphase high viscosity cosmetic preparation of the present invention comprises the major constituent of the cosmetic product and is incorporated to mold the hair and hold the hair in place during styling. In addition, the sculpting phase provides the hair with support or body for the particular style as well as imparting an overall, modification to the interfibril interaction of the hair. As mentioned above, the sculpting phase generally incorporates gel forming agents, setting types and film forming agents, and modifying agents and carriers.

In determining the preferred gel forming agents which will attain the desired gelling matrix, special attention must be paid to the rheological characteristics of the gel forming agent and the agent's ability to keep the glossing/conditioning phase separate and uniform within the product during the storage and shipping. Furthermore, the gel forming agent must be capable of maintaining the integrity of each component as well as maintain the shape, form, and separation of the phases under the variety of conditions which will be experienced during storage and shipment, as well as during use.

In the preferred embodiment, it has been found that Carbomer 940 has the most desirable characteristics for the gel forming agent of this invention. However, other gel forming agents having the proper rheological characteristics and can be used. Substantially equivalent substitutes are Carbomer 934, Carbomer 941, hydroxypropyl cellulose, hydroxypropyl guar, hydroxyethyl cellulose, carboxymethyl cellulose, hydroxypropylmethyl cellulose, acrylates/steareth-20 methacrylate copolymer, silica, sodium stearate, and petrolatum. In addition, other similar products can be employed, generally depending upon the consistency of these product and the other components incorporated into this phase.

The preferred setting-film forming agent is a polyvinylpyrrolidone vinyl acetate copolymer (PVP/VA). This copolymer is preferred for its effectiveness in producing setting films of the type desired for this multiphase product. However, if desired, other copolymers of this type as well as various other setting film resins could be employed, without departing from the scope of this invention. Such other setting resins include sodium polystyrene sulfonate, polyvinylpyrrolidone/dimethylaminoethylmethacrylate copolymer, polymethylvinylether/maleic anhydride copolymer, adipic acid/epoxypropyl diethylenetriamine copolymer, and polyvinylpyrrolidone.

The remaining principal ingredients of the sculpting phase of the multi-phase cosmetic preparation of this invention are the modifying agents and carriers. These agents can be varied in their use or in the amount of products employed, depending upon the particular effects desired by the final composition. In the preferred embodiment, a neutralizing agent, such as triethanolamine, tetrahydroxypropyl ethylenediamine, amino methyl propanol, sodium hydroxide, or other appropriate agents are employed in order to raise or lower the pH of the final composition to either neutralize the rheological additives to obtain the proper viscosity or to neutralize the setting film forming agent and gain the proper solubility or set retension qualities.

Another modifying agent preferably incorporated into the composition is a film modifier to adjust the flexibility and moisture content within the film forming resin. Such modifiers as methyl gluceth-20, diethyl phthalate, phenyl trimethicone, soy bean oil, acetamide MEA or other similar agents are preferably employed in order to modify the film hardness and attain the desired flexibility, leveling, cohesion and adhesion of the composition and attain the desired setting, styling and hair handling properties being sought.

In addition, volatile or nonvolatile carriers or solvent systems can be incorporated to dissolve, disperse and/or adjust leveling and drying time as well as adjust the dry down feel, adhesion and rheological characteristics of the wet and dried product. Examples of such carriers are water, alcohol, isoparaffin, cyclomethicone, propylene glycol and other similar compounds. In addition, other modifying ingredients or agents may be incorporated into the sculpting phase, without departing from the scope of the present invention.

GLOSSING/CONDITIONING PHASE

As discussed above, the glossing/conditioning phase preferably comprises an opaque gel formed from a detactifying and glossing polymer along with dispersing agents, all of which are combined in a matrix of a gelling agent. The gelling matrix employed is important since it must maintain the integrity of the glossing/conditioning phase, as well as maintaining shape, form and separation from the sculpting phase.

The preferred gelling agent employed for the glossing/conditioning phase of the present invention is Carbomer 940. However Carbomer 940 is not the only rheological additive that can provide the necessary rheology in order to attain the desired viscosity, suspension of the active ingredients, and feel throughout the life span of the product in the container. Other additives that can be used with substantially equal efficacy are Carbomer 934, Carbomer 941, hydroxypropyl cellulose, hydroxypropyl guar, hydroxyethyl cellulose, carboxymethyl cellulose, hydroxypropylmethyl cellulose, acrylates/steareth-20 methacrylate copolymer, silica, sodium stearate, and petrolatum.

The gelling matrix also preferably incorporates a neutralizing agent, such as triethanolamine, tetrahydroxypropyl ethylenediamine, amino methyl propanol, sodium hydroxide, or other similar agents. By employing such neutralizing agents, the pH of the gelling matrix can be raised or lowered in order to either neutralize the rheological additive to attain proper viscosity or to neutralize the film forming agents to gain proper solubility or retention qualities.

In addition to the gel forming agents, the glossing/conditioning phase of the present invention also incorporates film forming or modifying agents, solvents and carriers, detactifying, glossing or lustering aids, and hair enhancing and sequestering agents.

Preferably, the film forming or modifying agents employed in the glossing/conditioning phase of the present invention comprises a water dispersible fatty agent such as ceteth-20, polysorbate-20, laureth-23, oleth-10, oleth-20, and myreth 3-laurate, and other similar compounds. These agents function as film and hand modifiers, as well as leveling aids, dispersing aids and a resolubilizer for aiding removal from the hair. In addition, glycerine and styrene/acrylate copolymers can also be employed as modifying agents.

In order to provide detactifying, glossing or lusterizing aids to the glossing/conditioning phase of the present invention incorporates water dispersible or insoluble materials which function as moisture barriers in conjunction with humectants to provide a balance of moisture/nonmoisture feel and interaction, as well as glossing. Such agents include dimethicone, mineral oil, almond oil, pentaerythritol tetrapelargonate, isopropyl myristate, myristylmyristate, isostearyl alcohol, cetearyloctanoate, cetyl alcohol, and the like. In addition, other water insoluble compositions and glossing aids could also be used with equal efficacy, without departing from the scope of the present invention. Other moisturizing agents or humectants, and sheen modifiers can be incorporated. Among the preferred agents are glycerin, propylene glycol, polyethylene glycol, sorbitol, and panthenol. If desired, hair enhancing and sequestering agents such as herbal extracts, preservatives, and fragrances can also be incorporated into the glossing/conditioning phase of the present invention.

Finally, volatile or non-volatile carriers or solvent systems are employed in order to dissolve, disperse and/or to adjust leveling and drying time as well as adjust dry down feel, adhesion and rheological characteristics of the wet and dried product. Examples of such carriers or solvents are water, alcohol, isoparaffin, cyclomethicone, propylene glycol and other similar compounds.

BEST MODE FOR CARRYING OUT THE INVENTION

In the tables set out below, preferred formulations for some of the various multi-phase, high viscosity cosmetic preparations of the present invention are presented in detail. As is apparent from these detailed disclosures, some exemplary uses for the multi-phase high viscosity cosmetic preparations of this invention are styling and conditioning agents, shampoos combined with conditioners, and hair, body and hand creams employing two distinct conditioning compositions.

By employing the teaching of the present invention, a variety of cosmetic preparations are attained wherein a single container is achieved capable of dispensing two or more independent, complementary cosmetic preparations simultaneously from a single container in a repeatable, consistent and metered ratio. In this way, complete repeatability and control of using precisely identical amounts of each product or phase each and every time is assured.

In Table I, the range of concentrations is provided for each of the preferred ingredients forming each of the two phases of the combined styling and conditioning product. In Tables II and III, the preferred formulations for each of the phases is separately detailed.

As is readily apparent from this disclosure, various compounds employing the preferred compositions can be eliminated, or if desired, substituted by altering similar compositions. Consequently, Tables I, II, and III are considered as examples of preferred compositions and are not intended in any way to limit the scope of the present invention.

TABLE I

| Multi-Phase High Viscosity Styling and Conditioning Product | |
|---|---|
| | % By Weight |
| Sculpting Phase | |
| Gel Forming Agents | 0.1–10 |
| Setting Resins | 0.1–20 |
| Modifying Agents | 0.001–40 |
| Solvents and Carriers | 20.0–95 |
| Detactifying, Glossing or Lusterizing Agents | 0–50 |
| Hair Enhancing and Sequestering Agents | q.s. to 100% |
| Glossing/Conditioning Phase | |
| Gel Forming Agents | 0.1–10 |
| Film Forming or Modifying Agents | 0.01–50 |
| Solvents and Carriers | 20. to 95 |
| Detactifying, Glossing or | |

TABLE I-continued

Multi-Phase High Viscosity Styling and Conditioning Product

| | % By Weight |
|---|---|
| Lusterizing Agents | 0.1–20 |
| Hair Enhancing and Sequestering Agents | q.s. to 100% |

In both the sculpting phase and the glossing/conditioning phase detailed in Table I, the preferred composition for the gel forming agents comprises a rheological additive ranging between about 0.1 and 5% by weight and a neutralizing agent ranging between about 0.01 and 5% by weight. Preferably, the rheological additive comprises at least one selected from the group consisting of Carbomer 940, Carbomer 934, Carbomer 941, hydroxypropyl cellulose, hydroxypropyl guar, hydroxyethyl cellulose, carboxymethyl cellulose, hydroxypropylmethyl cellulose, acrylates/steareth-20 methacrylate copolymer, silica, sodium stearate, and petrolatum. The preferred neutralizing agent comprises at least one selected from the group consisting of triethanolamine, tetrahydroxypropyl ethylenediamine, amino methyl propanol, and sodium hydroxide.

The setting resin incorporated into the sculpting phase preferably comprises at least one selected from the group consisting of polyvinylpyrrolidone vinylacetate copolymer (PVP/VA), sodium polystyrene sulfonate, polyvinylpyrrolidone/dimethylaminoethylmethacrylate copolymer, polymethylvinylether/maleic anhydride copolymer, adipic acid-epoxypropyl diethylenetriamine copolymer, and polyvinylpyrrolidone.

In addition, both the sculpting phase and the glossing/conditioning phase incorporate at least one modifying agent, preferably selected from the group consisting of glycerin, methyl gluceth-20, diethyl phthalate, phenyl trimethicone, soy bean oil, and acetamide MEA.

In the glossing/conditioning phase of the present invention, the film modifying agent incorporated therein preferably comprises at least one selected from the group consisting of Ceteth-20, glycerine, styrene/acrylate copolymer, polysorbate-20, laureth-23, oleth-10, oleth-20, and myreth 3-laurate.

In both the sculpting phase and the glossing/conditioning phase of the styling and conditioning preparation of the present invention, the solvents and carriers preferably employed comprise at least one selected from the group consisting of water, alcohol, propylene glycol, isoparaffin and cyclomethicone. In addition, the detactifying glossing or lusterizing aids preferably comprise at least one selected from the group consisting of dimethicone, myreth 3-laurate, panthenol, glycerin, propylene glycol, polyethylene glycol, sorbitol, mineral oil, almond oil, pentaerythritol tetrapelargonate, isopropyl myristate, myristylmyristate, isostearyl alcohol, cetearyloctanoate, and cetyl alcohol.

By referring to Table II, the preferred composition for the sculpting phase of the multi-phase, high viscosity styling and conditioning product of the present invention is provided in detail, while Table III details the preferred composition for the glossing and conditioning phase.

TABLE II

SCULPTING PHASE

| | % By Weight |
|---|---|
| Carbomer 940 | 0.9 |
| Triethanolamine | 0.95 |
| PVP/VA Copolymer | 14.0 |
| Methyl Gluceth-20 | 0.1 |
| SD Alcohol 40 | 30.0 |
| Water | 53.999529 |
| Tetradosium EDTA | 0.05 |
| D&C Yellow No. 10 | 0.000091 |
| FD&C Blue No. 1 | 0.00038 |

TABLE III

GLOSSING/CONDITIONING PHASE

| | % By Weight |
|---|---|
| Carbomer 940 | 0.90 |
| Triethanolamine | 0.90 |
| Ceteth-20 | 0.1 |
| Glycerin | 0.50 |
| Styrene/Acrylate Copolymer | 0.50 |
| Water | 94.997 |
| Dimethicone | 1.0 |
| Myreth 3-Laurate | 0.5 |
| Panthenol | 0.05 |
| Extract of Irish Moss | 0.001 |
| Extract of Clover Blossom | 0.001 |
| Extract of Bay Laurel | 0.001 |
| Tetrasodium EDTA | 0.05 |
| Fragrance | 0.50 |
| Methylchloroisothiazolinone and Methylisothiazolinone | 0.06 |

In the preferred consumer product, the ratio of the two independent phases is precisely controlled. In order to assure that the desired functional effect and visual appeal of each phase is attained, the concentrations of each of the ingredients in each phase was precisely determined, along with the mass ratio of the opaque phase to the clear phase. In this way, a distinctive visually perceivable multi-phase product is provided.

Using the sculpting phase found in Table II and the glossing/conditioning phase found in Table III, the ratio of the sculpting phase to the glossing/conditioning phase is preferably 75% to 25% by weight. In addition to the visual effect attained by this ratio, the concentration of all the ingredients of each of the phases has been found to provide the desired activity and function. Based upon extensive testing which has been performed, it has been found that the ratio of the phases can be adjusted along with varying the active concentration of the ingredients of each phase in order to attain a final product which will impart special effects to the hair as well as to attain a particular formulation for various hair types, such as coarse, wiry, permed and fine or limp hair.

In attaining the desired visual effect, the stripes formed from the opaque phase are preferably placed against the wall of a transparent container. In this way, the continuous or transparent phase is excluded from that portion of the container wall, thereby providing a clear, bright striped effect as well as an enhancement of the contrast of the stripes on the extruded, dispensed product.

Originally, round stripes of about one-quarter inch in diameter were employed and were found to be acceptable, providing good contrast both in the package and in the dispensed product. However, it has been found that flatter stripes, approximately 6 millimeters by 15 millimeters, provide a better final configuration. By employing flatter stripes, more contact with the container wall is attained and greater visual appearance on the outside of the extruded product is also realized.

In order to determine the preferred visual appearance, independent stripes numbering between 1 and 4 were evaluated. In these tests, both clear and opaque stripes were employed. In the preferred embodiment, three symmetrical stripes are employed, using the opaque phase of the product, with the stripes being placed directly against the outside wall of the transparent container, longitudinally aligned with the central axis of the container. In this way, a full view of all three stripes is attained regardless of the angle of viewing, with complete visibility of the stripes through the clear phase also being realized.

Finally, both laminated, non-memory tubes were employed as well as piston pump dispensers. In the preferred product, wherein three opaque stripes are employed along with a clear continuous gel phase, the clear walled piston pump was found to be the most desirable.

When used by the consumer, the final product also provides a visually aesthetic product when dispensed into the hand of the user, as a substantially continuous multi-phase product ribbon. In addition to the aesthetically pleasing multi-phase appearance of the product in the container, the product being dispensed into the hand of the user also imparts this same multi-phase aesthetically pleasing visual effect.

Once in the hand of the user, the product may be rubbed, or directly applied, depending upon the particular formulation of the product being used. In this way, the intermingling of the phases provides a further enhanced aesthetic effect as well as allowing two previously separate, independent products to be simultaneously dispensed and mixed in the palms or hands of the user, attaining a substantially homogeneous product, for application to the hair in the appropriate fashion as determined by the desired style or the cosmetoligist. As a result, previously separate products which would have to be carefully dispensed to attain the desired ratio are automatically dispensed simultaneously in a specifically metered amount in order to assure that the precise effect desired is consistently and repeatedly attained.

In addition to the multi-phase hair sculpting and glossing product detailed above, other cosmetic products can also be formulated in multi-phase high viscosity compositions. One such alternate cosmetic product is a hair shampoo combined with hair conditioners. In this way, hair cleansing compounds can be incorporated in one distinct phase, while specific hair conditioning agents can be incorporated in the alternate phase and provided in a multi-phase, high viscosity product for ease of dispensing, while also assuring the precisely desired metered ratio of each component phase. In Table IV, the overall composition for a shampoo and conditioner multi-phase high viscosity product is provided.

TABLE IV

SHAMPOO/CONDITIONERS

| Foaming and/or Emulsifying Agents | 1.0–18.0 |
| --- | --- |
| Viscosity and/or Foam Modifying Agents | 1.0–10.0 |
| Hair and Skin Modifying Agents | 0.2–90 |
| pH, Color, Preservation and Dilution Enhancing Agents | q.s. to 100% |

Using the product formulation detailed in Table IV, both the shampoo or cleansing phase as well as the conditioning phase may be constructed. In the preferred embodiment, one of the phases would be made transparent or clear, while the other phase would be opaque. Furthermore, by changing the relative ratios of each of the ingredients, particularly making the conditioning phase higher in oils and waxes, or other conditioning and modifying ingredients, the desired dual-phase, dual-purpose product composition can be attained.

In the preferred constructions, the foaming and emulsifying agents preferably comprise anionic, cationic, nonionic or Zwitterionic surfactants. Included in such surfactants would be at least one selected from the group consisting of sodium lauryl sulfate and glycerylmonostearate.

The viscosity and foam modifying agents incorporated into the shampoo/conditioner composition preferably comprises at least one selected from the group consisting of amides, amine oxides, hydroxypropylmethylcellulose, silica, acrylate/steareth-20 methacrylate copolymer. Finally, the hair and skin modifying agents preferably comprise at least one selected from the group consisting of quats, polyquaternium 5, polyquaternium 7, polyquaternium 10, polyanionics, oils, esters, silicones, dimethicones, and waxes.

In the preferred embodiment, the multi-phase, high viscosity shampoo and conditioner of the present invention comprises a cleansing phase having the composition detailed in Table V. In addition, the conditioning phase of the multi-phase high viscosity shampoo and conditioning product comprises the formulation detailed in Table VI.

It has been found that by employing the illustrative formulations detailed in Table V and Table VI, a unique, multi-phase, high viscosity shampoo and conditioner can be attained which is capable of precisely dispensing the desired metered ratio amounts of both the cleansing phase and conditioning phase, while still providing both an opaque phase and a substantially clear phase assuring the aesthetic, unique features of this invention.

TABLE V

CLEANSING PHASE

|  | % By Weight |
| --- | --- |
| Ammonium Lauryl Sulfate | 30.0 |
| Cocamidopropyl Betaine | 6.0 |
| Lauramide DEA | 2.0 |
| Hydroxypropylmethylcellulose | 0.5 |
| D&C Yellow No. 10 | 0.0001 |
| Lactic Acid | 0.1 |
| Methylchloroisothiazolinone and Methylisothiazolinone | 0.06 |
| Water | 61.3399 |

TABLE VI

CONDITIONING PHASE

|  | % By Weight |
| --- | --- |
| Glyceryl Monostearate | 3.0 |
| Sodium Steareth Sulfate | 1.0 |
| Hydroxypropylmethylcellulose | 0.5 |
| Cetyl Alcohol | 3.0 |
| Stearalkonium Chloride | 3.0 |
| Polyquaternium 10 | 0.2 |
| Lactc Acid | 0.1 |
| Methylchloroisothiazolinone and Methylisothiazolinone | 0.6 |
| Water | 89.14 |

Another multi-phase, high viscosity cosmetic product capable of incorporating the teaching of the present invention comprises multi-purpose conditioners formulated for hair, body or hand creams. By incorporating the teaching of this invention, two separate and distinct conditioners can be incorporated into a single product to provide a precise, measured, metered ratioed quantity of each phase to the user, each time the product is dispensed from the container. In this way, a hair, body or hand cream composition having a unique blend of conditioners previously incapable of being incorporated into a single product can be attained.

For exemplary purposes, Table VII defines the overall composition for the two, independent conditioners formulated for providing the desired resulting composition for a hair, body or hand cream product.

TABLE VII

CONDITIONER/CONDITIONER FOR HAIR, BODY, OR HAND CREAM PRODUCTS

| Conditioner "A" | Conditioner "B" |
|---|---|
| Emulsifier/Conditioner | Emulsifier/Conditioner |
| Stearalkonium Chloride, Quats | Mineral Oil Petrolatum |
| Viscosity Builder | Viscosity Builder |
| Stearyl Alcohol | Beezwax Silica Ozokerite Stearyl alcohol Sodium stearate |
| Diluent | Diluent |
| Water, isoparaffin, cyclomethicone | Water, isoparaffin, cyclomethicone |

As is apparent from the preceding description, a variety of multi-phase, high viscosity cosmetic products can be attained incorporating the teaching of the present invention. Although hair styling and glossing products, as well as shampoos and hair, body or hand cream products have been detailed, a variety of other cosmetic products can be prepared using the teaching of the present invention without departing from the scope of this invention.

It will thus be seen that the objects set forth above, among those made apparent from the preceding description, are efficiently attained and, since certain changes may be made in the above products, without departing from the scope of this invention, it is intended that all matter contained in the above descriptive shall be interpreted as illustrative and not in a limiting sense.

It is also to be understood that the following claims are intended to cover all of the generic and specific features of the invention hereindescribed, and all statements of the scope of the invention which, as a matter of language, might be said to fall therebetween.

Particularly, it is to be understood that the following claims, ingredients or compounds recited in the singular are intended to include compatible mixtures of such ingredients, wherever the sense permits.

Having described our invention, what we claim as new and desire to secure by Letters Patent is:

1. A cosmetic product for application to the hair comprising a hair styling phase and a hair conditioning phase formed as two separate, distinct, and independent phases each of which is stored in contact with each other in a single container with each of said phases comprising a gelling matrix for retaining each phase rheologically separate and distinct from its adjacent phase said gelling matrix comprising A. at least one gelling agent selected from the group consisting of carbomer 940, carbomer 934, carbomer 941, hydroxypropyl cellulose, hydroxypropyl guar, hydroxethyl cellulose, carboxymethyl cellulose, hydroxypropylmethyl cellulose, acrylates/steareth-20 methacrylate copolymer, silica, sodium stearate, and petrolatum, and B. at least one neutralizing or pH adjusting agent selected from the group consisting of triethanolamine, tetrahydroxypropyl ethylenediamine, amino methyl propanol, and sodium hydroxide; whereby previously incompatible compounds are capable of being packaged in a single container and simultaneously dispensed therefrom in a pre-set metered ratio.

2. A combined hair styling and conditioning product incorporating two separate, distinct and independent phases each of which are stored in contact with each other in a single container for being dispensed simultaneously therefrom in a particular metered ratio, said phases being further defined as comprising A. a sculpting phase incorporating
   a. between about 0.1 and 10% by weight of a gel forming matrix comprising at least one selected form the group consisting of carbomer 940, carbomer 934, carbomer 941, hydroxypropyl cellulose, hydroxypropyl guar, hydroxyethyl cellulose, carboxymethyl cellulose, hydroxypropylmethyl cellulose, acrylates/steareth-20 methacrylate copolymer, silica, sodium stearate, and petrolatum, and at least one neutralizing agent comprising at lease one selected from the group consisting of triethanolamine, tetrahydroxypropyl ethylenediamine, amino methyl propanol, and sodium hydroxide;
   b. between about 0.1 and 20% by weight of a setting resin comprising at least one selected from the group consisting of polyvinylpyrrolidone vinyl acetate copolymer, sodium polystyrene sulfonate, polyvinylpyrrolidone/dimethylaminoethylmethacrylate copolymer, polymethylvinylether/maleic anhydride copolymer, adipic acid/epoxypropyl diethylenetriamine copolymer, and polyvinylpyrrolidone;
   c. between about 0.001 and 40% by weight of at least one modifying agent comprising one selected from the group consisting of methyl gluceth-20, diethyl phthalate, phenyl trimethicone, soy bean oil, and acetamide MEA;
   d. between about 20 and 95% by weight of at least one solvent or carrier comprising a volatile or non-volatile composition employed to dissolve, disperse and adjust leveling and drying time as well as dry down feel, adhesion and rheological characteristics of the final product and comprising one selected from the group consisting of water, alcohol, isoparaffin, cyclomethicone, and propylene glycol;
   e. between about 0 and 50% by weight of at least one detactifying, glossing or lustering agent comprising water dispersible or insoluble materials functioning as moisture barriers in conjunction with humectants to provide a balance of moisture/nonmoisture feel and interaction; and B. a glossing/conditioning phase incorporating
   a. between about 0.1 and 10% by weight of a gel forming matrix comprising at least one selected from the group consisting of carbomer 940, carbomer 934, carbomer 941, hydroxypropyl cellulose, hydroxypropyl guar, hydroxyethyl cellulose, carboxymethyl cellulose, hydroxypropylmethyl cellulose, acrylates/steareth-20 methacrylate copolymer, silica, sodium stearate, and petrolatum, and at least one neutralizing agent comprising at least one selected from the group consisting of triethanolamine, tetrahydroxypropyl ethylenediamine, amino methyl propanol, and sodium hydroxide;

b. between about 0.01 and 50% by weight of at least one film forming or modifying agent comprising a water dispersible fatty agent which functions as a film modifier, leveling aid, dispersing aid and a resolubilizer for aiding removal from the hair;

c. between about 20 and 95% by weight of at least one solvent or carrier comprising a volatile or non-volatile composition employed to dissolve, disperse and adjust leveling and drying time as well as dry down feel, adhesion and rheological characteristics of the final product and comprising one selected from the group consisting of water, alcohol, isoparaffin, cyclomethicone, and propylene glycol; and d. between about 0.1 and 20% by weight of at least one detactifying, glossing or lustering agent comprising water dispersible or insoluble materials functioning as moisture barriers in conjunction with humectants to provide a balance of moisture/nonmoisture feel and interaction; whereby a unique styling and conditioning product is attained wherein two separate and independent phases of a high viscosity cosmetic preparation are capable of being housed in a single container and simultaneously dispensed in a specific, desired metered ratio, upon actuation of the dispensing container.

3. The combined styling and conditioning product defined in claim 2, wherein one of said phases is further defined as being opaque, and said other phase is substantially transparent or translucent, thereby providing a distinct, visual contrast between said phases.

4. The combined styling and conditioning product defined in claim 2 wherein said gel forming agent is further defined as comprising between about 0.1 and 5% by weight, and said neutralizing agent comprises between about 0.01 and 5% by weight.

5. The combined styling and conditioning product defined in claim 2, wherein said film forming or modifying agent is further defined as comprising at least one selected from the group consisting of ceteth-20, polysorbate-20, laureth-23, oleth-10, oleth-20, and myreth 3-laurate, glycerine and styrene/acrylate copolymers.

6. The combined styling and conditioning preparation defined in claim 2, wherein said detactifying, glossing or lusterizing agent is further defined as comprising at least one selected from the group consisting of dimethicone, mineral oil, almond oil, pentaerythritol tetrapelargonate, isopropyl myristate, myristylmyristate, isostearyl alcohol, cetearyloctanoate, cetyl alcohol, glycerin, propylene glycol, polyethylene glycol, sorbitol, and panthenol.

7. The combined styling and conditioning preparation defined in claim 2, wherein the sculpting phase and the glossing/conditioning phase are further defined as comprising hair enhancing and sequestering-related agents selected from the group consisting of herbal extracts, preservatives, chelating agents, and fragrances.

8. The combined styling and conditioning product defined in claim 2, wherein the ratio of the quantity of the sculpting phase relative to the glossing/conditioning phase comprises about 3 to 1.

9. A combined styling and conditioning product incorporating two separate, distinct, and independent phases each of which are stored in contact with each other in a single container for being simultaneously dispensed therefrom, and comprising A. a sculpting phase which consists essentially of
 a. about 1% by eight of Carbomer 940,
 b. about 1% by weight of triethanolamine,
 c. about 14% by weight of polyvinylpyrrolidone vinyl acetate copolymer,
 d. about 0.1% by weight of methyl gluceth-20,
 e. about 30% by weight of alcohol,
 f. about 54% by weight of water, and
 g. trace amounts of Tetradosium EDTA, D&C Yellow No. 10 and FD&C Blue No. 1; and B. a glossing/conditioning phase consisting essentially of
 a. about 1% by weight of Carbomer 940,
 b. about 1% by weight of triethanolamine,
 c. about 0.1% by weight of Ceteth-20,
 d. about 0.5% by weight of glycerin,
 e. about 0.5% by weight of styrene/acrylate copolymer,
 f. about 95% by weight of water,
 g. about 1% by weight of dimethicone,
 h. about 0.5% by weight of myreth 3-laurate,
 i. about 0.05% by weight of panthenol,
 j. about 0.05% by weight of tetrasodium EDTA,
 k. about 0.5% by weight of a fragrance,
 l. about 0.06% by weight of methylchloroisothiazolinone and methylisothiazolinone, and
 m. trace amounts of extract of irish moss, extract of clover blossom and extract of bay laurel.

10. A combined shampoo and conditioning product incorporating two separate, distinct, and independent phases each of which are stored in contact with each other in a single container for being simultaneously dispensed therefrom, and comprising A. a shampoo or cleansing phase which consists essentially of
 a. about 30% by weight of ammonium lauryl sulfate;
 b. about 6% by weight of cocamidopropyl betaine;
 c. about 2% by weight of lauramide DEA;
 d. about 0.5% by weight of hydroxypropylmethylcellulose;
 e. about 0.1% by weight of one selected from the group consisting of lactic acid and triethanolamine;
 f. about 0.06% by weight of methylchloroisothiazolinone and methylisothiazolinone,
 g. trace amounts of D&C Yellow No. 10;
 h. water forming the balance; and B. a conditioning phase consisting essentially of
 a. about 3% by weight of glyceryl monostearate;
 b. about 1% by weight of sodium steareth sulfate;
 c. about 0.5% by weight of hydroxypropylmethylcellulose;
 d. about 3% by weight of cetyl alcohol;
 e. about 3% by weight of stearalkonium chloride;
 f. about 0.2% by weight of polyquaternium 10;
 g. about 0.1% by weight of one selected from the group consisting of lactic acid and triethanolamine;
 h. about 0.6% by weight of methylchloroisothiazolinone and methylisothiazolinone; and
 i. water forming the balance.

* * * * *